United States Patent [19]
Madlener

[11] 4,123,046
[45] Oct. 31, 1978

[54] DEVICE FOR SECURING A MIXING CAPSULE FOR DENTAL PREPARATIONS

[75] Inventor: Bruno A. Madlener, Feldkirch-Tosters, Austria

[73] Assignee: Etablissement Dentaire Ivoclar, Schaan, Liechtenstein

[21] Appl. No.: 810,813

[22] Filed: Jun. 28, 1977

[30] Foreign Application Priority Data
Jul. 6, 1976 [DE] Fed. Rep. of Germany ....... 2630376

[51] Int. Cl.² .............................................. B25B 5/14
[52] U.S. Cl. .................................................. 269/228
[58] Field of Search ................ 269/228, 211, 254 CS; 259/72, 91, DIG. 20

[56] References Cited
U.S. PATENT DOCUMENTS

| 408,473 | 8/1889 | Focken | 269/211 |
|---|---|---|---|
| 2,379,107 | 6/1945 | Scheck | 269/228 |
| 3,578,307 | 5/1969 | Lock | 269/96 |
| 3,749,390 | 7/1973 | Schubert | 269/254 CS |

Primary Examiner—Robert C. Watson
Attorney, Agent, or Firm—Burgess, Dinklage & Sprung

[57] ABSTRACT

An improvement in a device for securing a mixing capsule for dental preparations to the support of a vibrating machine for mixing the components of said dental preparations, the device being improved in that said support is provided with an abutment and a presser adjustable by a toggle lever pivoted to said support connected by way of a link to said presser which presser is axially movable in a reciprocating manner and in relation to said abutment.

11 Claims, 6 Drawing Figures

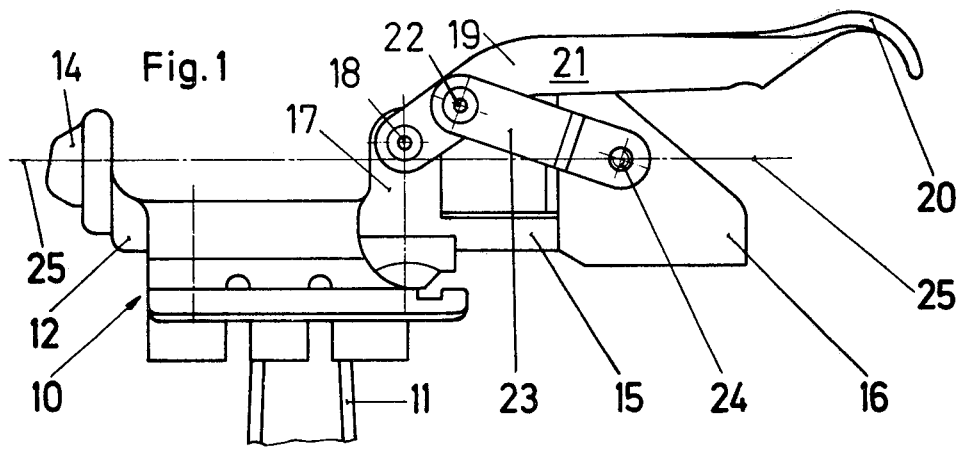
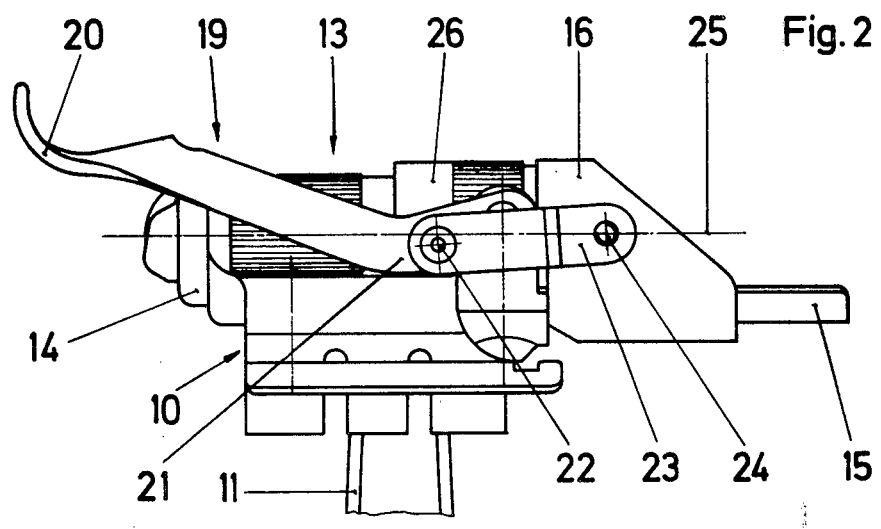
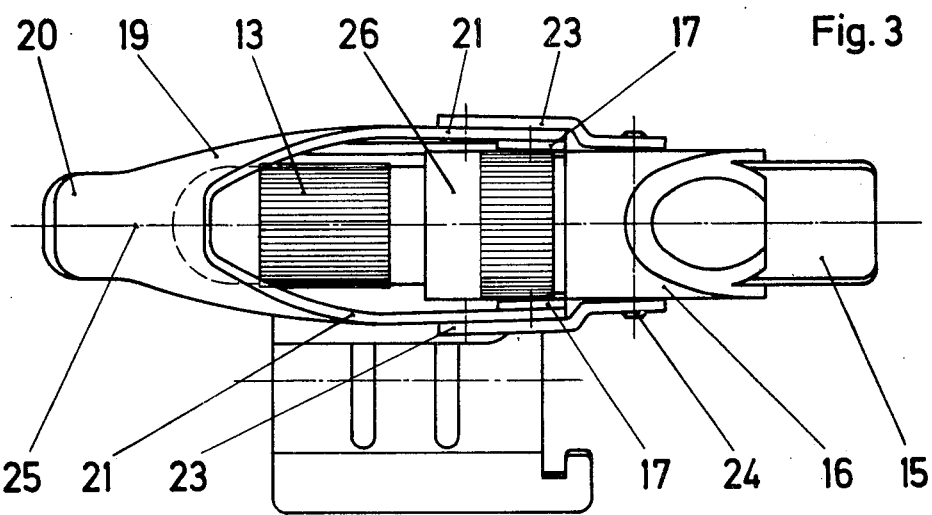

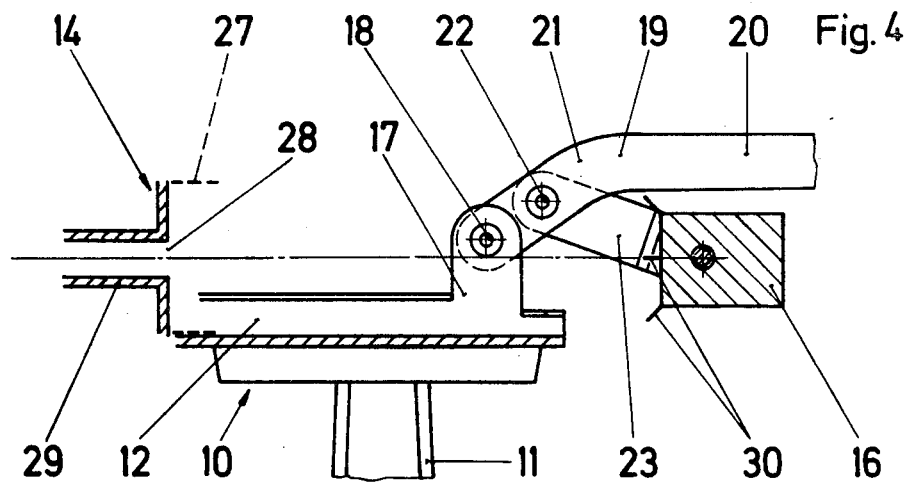
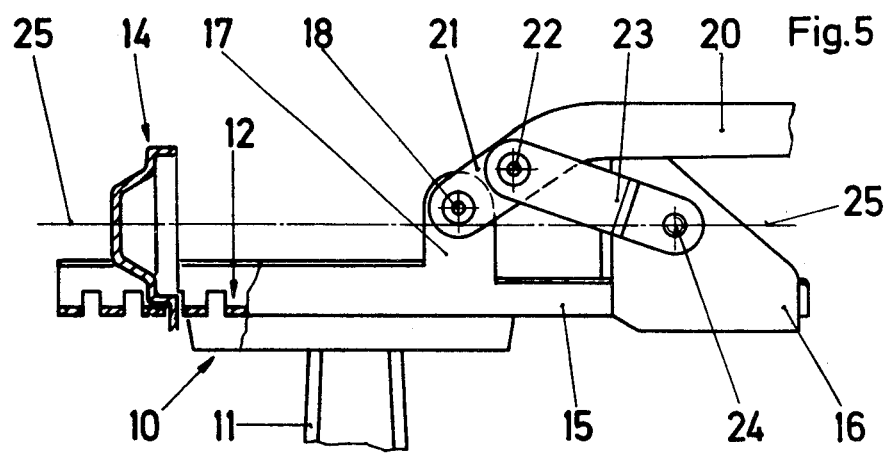
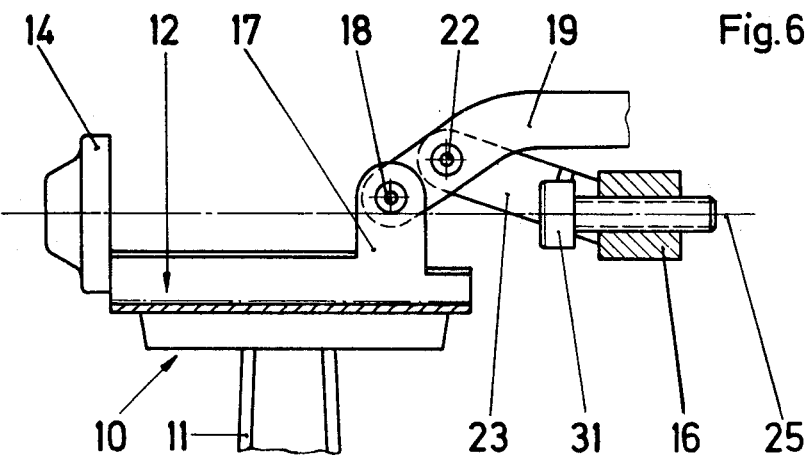

DEVICE FOR SECURING A MIXING CAPSULE FOR DENTAL PREPARATIONS

BACKGROUND OF THE INVENTION

1. Field of the Invention

The invention relates to a device for securing a mixing capsule for dental preparations to the support of a vibrating machine for mixing the components of said dental preparations, said support being provided with an abutment and a presser adjustable by an operating lever pivoted to said support, said abutment and said presser being adapted to secure said mixing capsule in a first position of said presser and to release said mixing capsule in a second position of said presser.

2. Discussion of the Prior Art

To mix dental preparations consisting of at least two components, such as amalgam, vibrating machines are known which can vibrate one mixing capsule at a time at a high frequency for a predetermined time; the various components experience thorough mixing to give an end product in the form of a tooth filling composition. Most of the known vibrating machine constructions comprise a rocking arm having two spring strips arranged like a fork, the spring strip ends having holders or the like for the capsule as shown e.g. in the U.S. Pat. No. 3,222,037. The swing arm is mounted at one end and can be vibrated multidimensionally by one-dimensional or multi-dimensional eccentric drives; preferred directions of vibration can be determined by the mounting of the swing arm and by the use of at least one stabilizing spring.

It is also known to provide a carrier or support for the mixing capsule on the swing arm. The carrier has a stationary abutment and an adjustable presser which either takes the form of an adjusting screw to press the mixing capsule towards the abutment or is a two-armed lever, one arm of which presses on one end of the capsule when the other arm experiences a corresponding lever-pivoting force. For this purpose, the other lever arm of the known device has a sliding surface engaged by an eccentric secured by way of an operating lever to a spindle rotatably mounted on the carrier or support. The capsule is placed against the abutment to locate it, whereafter the two-armed lever pivots towards the other end of the capsule, and when the operating or control lever is pressed down manually, the eccentric presses against the sliding surface on the other arm of the two-armed lever until the capsule has been located on the carrier or support. The tightness of the securing or clamping depends upon frictional engagement between the eccentric and the sliding surface. The frictional engagement is increased by the weight of the actuating or operating lever. However, this is no guarantee of the capsule continuing to remain located when subjected to multidimensional vibratory motion. The operating lever itself has a considerable mass which can make natural vibrations, which can lead to the two-armed lever working loose or to the location of the capsule becoming ever tighter as a result of the eccentric becoming wedged more strongly relatively to the sliding surface. This may lead after prolonged use to a damage of the sliding surface and to the eccentric contact surface, and once the damage has occurred considerable clearance rapidly arises, making it impossible to locate the capsule satisfactorily and to remove the capsule from the support. The difficulty of removal is a particular disadvantage since the prepared filling should be applied very rapidly.

Another disadvantage of the known vibrating machines for mixing dental preparations is that, in the case of mixing capsules in which one component for the mix, e.g. mercury, is placed in a shallow pad-like foil bag or the like whose contents are introduced into the mixing chamber by adjustment of a cap relatively to the mixing capsule immediately before mixing, an extra appliance is required to open and empty the foil bag, and since considerable forces are required to make sure that the bag is emptied completely, the usual practice is to use a table appliance having a long enough lever arm to move the cap relatively to the capsule. The mixing capsule, which by now contains all the components in its mixing chamber, must then be inserted into and secured or located in the vibrating machine, special care being necessary to prevent any exit of mercury or mercury vapors during the preparation of amalgam fillings.

It is an object of this invention to provide a device enabling mixing capsules to be secured, with a tightness which remains constant, to the vibrating machine support so as to facilitate the individual mixing operation and to increase the working life of the system. Also, in the case of mixing capsules in which one component is stored in a foil bag, the manner in which the force is applied is such that the bag can be opened during the location of the capsule and the bag contents introduced into the capsule mixing chamber, thus obviating the need for the conventional extra appliance.

SUMMARY OF THE INVENTION

In accordance with the foregoing this invention broadly contemplates a device for securing a mixing capsule which provides an improved fixing and enables the opening of a foil bag during the location of the capsule. Hence, the present invention contemplates an improvement in a device for securing a mixing capsule for dental preparations to the support of a vibrating machine for mixing the components of said dental preparations, said support being provided with an abutment and a presser adjustable by an operating lever pivoted to said support, said abutment and said presser being adapted to secure said mixing capsule in a first position of said presser and to release said mixing capsule in a second position of said presser which device is improved in that said operating lever is a toggle lever connected by way of a link to the presser which presser is axially movable in a reciprocating manner and in relation to the abutment from its second position to its first position and vice versa.

The objects of this invention are provided, because the mixing capsule is secured very tightly to the support, since the link pivot point on the toggle overshoots a dead-center position when the mixing capsule is being located. The toggle closure applies maximum force to the capsule at the dead-center position and therebeyond there is a slight reduction of clamping which in itself is negligible but ensures that the capsule continues to remain secured to the support even when experiencing multi-dimensional vibrations. The fixing of the capsule therefore remains constant even when the capsules are curved and when they experience correspondingly set-up vibratory motions. Due to the disappearance of wearing friction surfaces, the device remains effective at a constant level even after prolonged intensive use. There is virtually no wear of the bearings although the toggle lever, the two links which it is convenient to use, the abutment and the presser can be relatively light sheet-metal parts. The complete device on the support is therefore of very low self-weight so that the vibrating masses can be small. The complete vibrating machine can therefore be of light weight construction. First costs and power consumption are less than for the known devices. The choice of vibration frequencies and the periods of vibration can be varied within wide limits. However, an optimum fixing force for the capsule is ensured despite the low self-weight of the device. Since the toggle fastening applies considerable tension to the presser via the links in the region immediately before the dead-center, a foil-bag can be opened and emptied during this phase of the movement; the arrangement can be such that, by the time the toggle fastener has reached its dead-center position, the bag has been completely emptied and its entire contents are in the capsule mixing chamber. The cap which usually extends around the foil bag is pressed against the capsule to ensure satisfactory sealing, thus ensuring that during the subsequent mixing step neither mercury nor vapors thereof, e.g. when amalgam is being used, can escape.

Since the capsules themselves have adequate dimensional stability, it is sufficient for the abutment just to have a guide retaining the capsule in a particular alignment. The presser can then be disposed without any special guide at the free end of the two links. Conveniently, however, the presser is mounted for movement on a rail of the support, no special guides then being required in the stationary abutment. In both constructions the presser is bound to move linearly along the same axis as the one on which the center of the abutment or the axis of the capsule is disposed. The linear movement of the presser also permits a non-tilting movement of the cap relatively to the mixing capsule during the opening of the foil bag.

The device according to the invention is suitable for use with foil bags of a variety of thicknesses. To deal with capsules of different lengths, the presser can have an adjustable contact element or the abutment can be disposed for adjustment on the support.

BRIEF DESCRIPTION OF THE DRAWING

Referring to the accompanying drawings showing some preferred embodiments of the invention:

FIG. 1 is a side elevational view of the device in its second or releasing position and without a mixing capsule.

FIG. 2 is a side elevational view of the device in its first or securing position of a mixing capsule secured in the device.

FIG. 3 is a plan view of the device as shown in FIG. 2.

FIG. 4 is a diagrammatic view, partially in section, of another embodiment of the device.

FIGS. 5 and 6 are diagrammatic views, partially in section, of various details of other embodiments of the device for securing capsules of different lenths.

DESCRIPTION OF SPECIFIC EMBODIMENTS

FIG. 1 shows a first embodiment of the device, comprising a support or carrier 10 mounted on a rocking arm or swing arm 11 which extends out of a vibrating machine (not shown) of the kind hereinbefore described.

The support 10 has a trough-like bed 12 basically adapted to the cylindrical outside shape of a mixing capsule 13. The bed 12 is shallow enough for the capsule 13 to be gripped readily with two fingers of the hand. There is a stationary abutment 14 at one end of the bed 12 which at its other end extends into a relatively narrow guide rail 15 on which a presser 16 can reciprocate. A bearing arm 17 is connected at each side of the capsule 13 to the side edges of the bed 12. The trough-like bed 12, the abutment 14, the rail 15 and the two arms 17 can be a unitary metal construction. Disposed at the free ends of arms 17 are bearings 18 for a toggle lever 19 which has an operating arm or grip 20. Extending therefrom to the bearings 18 are, as can be seen in FIG. 3, two arms 21. In the manner conventional in toggle fastenings, bearings 22 for a link 23 are provided between the bearings 18 and the grip 20. The links 23 extend to bearings 24 on the presser 16.

When the device is in its second or releasing position shown in FIG. 1, a mixing capsule 13 is placed loosely in the bed 12. The grip 20 is grasped and the lever 19 is pivoted into its first or securing position shown in FIG. 2. Just before the bearings 22 of the link 23 reach a line 25 forming the central thrust line coinciding with the central axis of the capsule 13, the cap 26 of capsule 13 — if a pad-like foil bag containing one mixture component, such as mercury, is used — presses the bag open and so compresses it that the bag has been completely emptied at the latest by the time that the bearing 22 passes by the line 25. The bearings 22, which in FIG. 2 are below the line 25, prevent the toggle fastening from releasing, and therefore the capsules 13 from working loose, even under multidimensional vibrations superimposed upon another in any way.

Referring to the embodiment shown in FIG. 4, the abutment 14 has guides which align the capsule 13 relatively to the support 10 even when the toggle lever 19 pivots. The guides can take the form of a cylindrical extension 27 or of a bore 28 having a cylindrical extension 29 if tubular capsules are used which have an enlarged collar at one end to receive the cap 26 and the foil bag. In this embodiment, and as can be gathered from FIG. 4, no guide rail is required for the presser 16. It is sufficient for the same just to have projections 30 which provide some guiding of the presser 16 relatively to the cap 26 or capsule 13.

So that the device may be adapted to mixing capsules of different lengths, the abutment 14 can be mounted on the support 10 for axial movement, in the manner shown in FIG. 5. Alternatively, and as shown in FIG. 6, the presser 16 can have a contact element 31 movable axially relatively to the presser 16. The adjustable or moving elements can be designed to be adjusted in steps for predetermined capsule lengths. However, such adjustment can be stepless. Another way of providing stepwise adjustment (not shown) is for the presser 16 or the pair of links 23 to have a number of connection places for the pairs of links 23 or for the presser 16.

The links 23 and the toggle lever 19 can be made of thin-walled metal. The complete device therefore has a relatively reduced self-weight yet ensures an optimum fixing or locating force. The latter remains constant over a very long period of use although the toggle device is used in one phase of the movement of the toggle lever to open and empty a foil bag (if used). Although two facilities are combined in a single device, not only is there no increase in constructional outlay and vibrating masses, but there is even a simplification of constructional outlay and maintenance.

What is claimed is:

1. In a device for securing a mixing capsule for dental preparations to the support of a vibrating machine for mixing the components of said dental preparations, said support being provided with an abutment and a presser adjustable by an operating lever pivoted to said support, said abutment and said presser being adapted to secure said mixing capsule in a first position of said presser and to release said mixing capsule in a second position of said presser the improvement wherein said operating lever is a toggle lever connected by way of a link to the presser such that when said toggle lever is moved to dispose said presser from said second position to said first position the link pivot point on said toggle overshoots a dead center position, said presser being axially movable in a reciprocating manner and in relation to the abutment from its second position to its first position and vice versa, the central thrust line of the apparatus being coincident with the central axis of a capsule to be disposed therein.

2. A device according to claim 1 wherein said abutment has guide means which align the mixing capsule relatively to said presser even when said toggle lever is moved from its second position to its first position and vice versa.

3. A device according to claim 1 wherein said presser is mounted for movement on a guide rail extending from that end of said support being opposite to that end at which said abutment is provided.

4. A device for securing a mixing capsule for dental preparations to the support of a vibrating machine for mixing the components of said dental preparations, wherein said support has a bed which is adapted to receive said mixing capsule, said support being provided with an abutment and a presser adjustable by a toggle lever pivoted to said support, and wherein said presser is mounted for movement on a guide rail extending from that end of said support being opposite to that end at which said abutment is provided, said abutment and said presser being adapted to secure said mixing capsule in a first position of said presser and to release said mixing capsule in a second position of said presser, said toggle lever being connected by way of a link to said presser such that when said toggle lever is moved to dispose said presser from said second position to said first position the link point on said toggle overshoots a dead center position, said presser being axially movable in a reciprocating manner and in relation to said abutment from its second position to its first position and vice versa.

5. A device according to claim 4 wherein said presser has a contact element which can be brought into engagement with said mixing capsule and which is mounted for axial movement on said presser.

6. A device according to claim 4 wherein said abutment on said support is adjustable axially.

7. A device according to claim 5 wherein said contact element on said presser is adjustable continuously in adaptation to different predetermined lengths of said mixing capsule.

8. A device according to claim 5 wherein said contact element on said presser is adjustable stepwise in adaptation to different predetermined lengths of said mixing capsule.

9. A device according to claim 6 wherein said abutment is adjustable continuously in adaptation to different predetermined lengths of said mixing capsule.

10. A device according to claim 6 wherein said abutment is adjustable stepwise in adaptation to different predetermined lengths of said mixing capsule.

11. A dental vibrating apparatus for vibrating a dental filling composition maintained within a capsule in a support on said apparatus comprising means for effecting a vibratory motion, said means rigidly connected to a support, said support comprising a bed for accomodating a mixing capsule, said support being provided with an abutment and a presser adjustable by a toggle lever pivoted to said support when said presser is mounted wherein said presser is mounted for longitudinal movement on a guide rail extending from that end of said support which is opposite to that end at which said abutment is provided, said abutment and said presser being adapted to secure said mixing capsule in a first position of said presser and to release said mixing capsule in a second position of said presser, said toggle lever being connected by way of a link to said presser such that when said toggle lever is moved to dispose said presser from said second position to said first position the link point on said toggle overshoots a dead center position, said presser axially and longitudinally movable in a reciprocating manner and in relation to said abutment in its second position to its first position and vice versa.

* * * * *